(12) United States Patent
Shaanan et al.

(10) Patent No.: US 8,333,717 B1
(45) Date of Patent: Dec. 18, 2012

(54) TEST UNIT CARTRIDGE FOR ANALYTE TESTING DEVICE

(75) Inventors: Gad Shaanan, La Jolla, CA (US); Marc Goldman, San Diego, CA (US)

(73) Assignee: YofiMeter, LLC, La Jolla, CA (US)

( * ) Notice: Subject to any disclaimer, the term of this patent is extended or adjusted under 35 U.S.C. 154(b) by 0 days.

(21) Appl. No.: 13/308,137

(22) Filed: Nov. 30, 2011

Related U.S. Application Data

(63) Continuation of application No. 13/187,397, filed on Jul. 20, 2011, which is a continuation-in-part of application No. 13/165,621, filed on Jun. 21, 2011.

(51) Int. Cl.
*A61B 5/00* (2006.01)
*B65D 81/00* (2006.01)

(52) U.S. Cl. .......... 600/584; 600/575; 600/583

(58) Field of Classification Search ......... 600/573, 600/575, 583, 585, 584; 606/181–182
See application file for complete search history.

(56) References Cited

U.S. PATENT DOCUMENTS

| | | |
|---|---|---|
| 4,794,926 A | 1/1989 | Munsch et al. |
| 4,936,833 A | 6/1990 | Sams |
| 5,064,098 A | 11/1991 | Hutter, III et al. |
| 5,196,025 A | 3/1993 | Ranalletta et al. |
| 5,269,762 A | 12/1993 | Armbruster et al. |
| 5,322,511 A | 6/1994 | Armbruster et al. |
| 5,569,186 A | 10/1996 | Lord et al. |
| 5,637,095 A | 6/1997 | Nason et al. |
| 5,728,074 A | 3/1998 | Castellano et al. |
| 5,871,494 A | 2/1999 | Simons et al. |
| 5,971,941 A | 10/1999 | Simons et al. |
| 6,045,537 A | 4/2000 | Klitmose |
| 6,071,294 A | 6/2000 | Simons et al. |

(Continued)

FOREIGN PATENT DOCUMENTS

CA 2526543 1/2005

(Continued)

OTHER PUBLICATIONS

* "Accu-Chek Mobile System", Blood Glucose Meter, Roche LTD., Feb. 23, 2011, http://www.accu-check.co.uk/gb/products/metersystems/mobile.html.

(Continued)

*Primary Examiner* — Rene Towa
*Assistant Examiner* — Adam Eiseman
(74) *Attorney, Agent, or Firm* — Perkins Coie LLP

(57) ABSTRACT

A test unit cartridge for holding a plurality of test units includes a first test unit that contains a first analyte sensor and a second test unit that contains a second analyte sensor. The first and second analyte sensors use first and second reagents to detect first and second analytes, respectively. The first analyte is different from the second analyte and the first and second test units are functionally non-fungible. The plurality of test units can also include a third test unit that contains two analyte sensors having two reagents for detecting two different analytes using one fluid sample. A method of using the test unit cartridge is also described, which comprises loading the cartridge into an analyte testing device and cocking an actuator of the device that is configured to (i) expose an analyte sensor of a test unit, (ii) ready a lancet, and (iii) advance a lancet cartridge.

12 Claims, 3 Drawing Sheets

U.S. PATENT DOCUMENTS

| | | |
|---|---|---|
| 6,228,100 B1 | 5/2001 | Schraga |
| 6,332,871 B1 | 12/2001 | Douglas et al. |
| 6,364,889 B1 | 4/2002 | Kheiri et al. |
| 6,454,746 B1 | 9/2002 | Bydlon et al. |
| 6,468,287 B1 | 10/2002 | Baugh |
| 6,472,220 B1 | 10/2002 | Simons et al. |
| 6,474,219 B2 | 11/2002 | Klitmose et al. |
| 6,482,186 B1 | 11/2002 | Douglas et al. |
| 6,582,404 B1 | 6/2003 | Klitgaard et al. |
| 6,585,698 B1 | 7/2003 | Packman et al. |
| 6,616,616 B2 | 9/2003 | Fritz et al. |
| 6,783,537 B1 | 8/2004 | Kuhr et al. |
| 6,827,899 B2 | 12/2004 | Maisey et al. |
| 6,849,237 B2 | 2/2005 | Housefield et al. |
| 6,872,358 B2 | 3/2005 | Hagen et al. |
| 6,997,343 B2 | 2/2006 | May et al. |
| 7,025,774 B2 | 4/2006 | Freeman et al. |
| 7,066,909 B1 | 6/2006 | Peter et al. |
| 7,094,221 B2 | 8/2006 | Veasey et al. |
| 7,175,642 B2 | 2/2007 | Briggs et al. |
| 7,192,405 B2 | 3/2007 | DeNuzzio et al. |
| 7,198,615 B2 | 4/2007 | Langley et al. |
| 7,211,096 B2 | 5/2007 | Kuhr et al |
| 7,220,248 B2 | 5/2007 | Mernoe |
| 7,258,693 B2 | 8/2007 | Freeman et al. |
| 7,261,691 B1 | 8/2007 | Asomani |
| 7,291,132 B2 | 11/2007 | DeRuntz et al. |
| 7,344,507 B2 | 3/2008 | Briggs et al. |
| 7,360,045 B2 | 4/2008 | Maezawa |
| 7,430,825 B2 | 10/2008 | Vanek et al. |
| 7,534,226 B2 | 5/2009 | Mernoe et al. |
| 7,582,063 B2 | 9/2009 | Wurster et al. |
| 7,662,065 B1 | 2/2010 | Kahn et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,753,879 B2 | 7/2010 | Mernoe |
| 7,776,030 B2 | 8/2010 | Estes et al. |
| 7,785,288 B2 | 8/2010 | Mernoe et al. |
| 7,785,338 B2 | 8/2010 | Kuhr et al. |
| 7,789,859 B2 | 9/2010 | Estes et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,794,430 B2 | 9/2010 | Langley et al. |
| 7,828,528 B2 | 11/2010 | Estes et al. |
| 7,833,196 B2 | 11/2010 | Estes et al. |
| 7,848,765 B2 | 12/2010 | Phillips et al. |
| 7,879,026 B2 | 2/2011 | Estes et al. |
| 7,883,015 B2 | 2/2011 | Ackermann et al. |
| 7,887,511 B2 | 2/2011 | Mernoe et al. |
| 7,887,512 B2 | 2/2011 | Estes et al. |
| 7,887,682 B2 | 2/2011 | Wang et al. |
| 7,892,183 B2 | 2/2011 | Boecker et al. |
| 7,892,185 B2 | 2/2011 | Freeman et al. |
| 7,892,199 B2 | 2/2011 | Mhatre et al. |
| 7,914,742 B2 | 3/2011 | Arbogast et al. |
| 7,922,708 B2 | 4/2011 | Estes et al. |
| 7,922,971 B2 | 4/2011 | Bryer et al. |
| 7,935,063 B2 | 5/2011 | Roe |
| 7,935,076 B2 | 5/2011 | Estes et al. |
| 7,935,105 B2 | 5/2011 | Miller et al. |
| 7,938,803 B2 | 5/2011 | Mernoe et al. |
| 7,951,114 B2 | 5/2011 | Rush et al. |
| 7,955,791 B2 | 6/2011 | Dinello et al. |
| 7,967,784 B2 | 6/2011 | Pongpairochana et al. |
| 7,981,084 B2 | 7/2011 | Estes et al. |
| 7,981,102 B2 | 7/2011 | Patel et al. |
| 8,021,345 B2 | 9/2011 | Veasey et al. |
| 8,032,226 B2 | 10/2011 | Miller et al. |
| 8,057,436 B2 | 11/2011 | Causey et al. |
| 8,105,279 B2 | 1/2012 | Mernoe et al. |
| 8,109,921 B2 | 2/2012 | Estes et al. |
| 8,152,765 B2 | 4/2012 | Briones et al. |
| 8,192,394 B2 | 6/2012 | Estes et al. |
| 2002/0170823 A1 | 11/2002 | Housefield et al. |
| 2002/0177761 A1 | 11/2002 | Orloff et al. |
| 2003/0083685 A1 | 5/2003 | Freeman et al. |
| 2003/0153900 A1 | 8/2003 | Aceti et al. |
| 2003/0191415 A1 | 10/2003 | Moerman et al. |
| 2004/0044272 A1 | 3/2004 | Moerman et al. |
| 2004/0082878 A1* | 4/2004 | Baldwin et al. ............... 600/573 |
| 2004/0098009 A1 | 5/2004 | Boecker et al. |
| 2004/0127819 A1 | 7/2004 | Roe |
| 2004/0172284 A1 | 9/2004 | Sullivan et al. |
| 2005/0015020 A1 | 1/2005 | LeVaughn et al. |
| 2005/0227370 A1* | 10/2005 | Ramel et al. ................. 436/514 |
| 2005/0238538 A1 | 10/2005 | Braig et al. |
| 2006/0229502 A1 | 10/2006 | Pollock et al. |
| 2006/0245131 A1 | 11/2006 | Ramey et al. |
| 2006/0279431 A1 | 12/2006 | Bakarania et al. |
| 2006/0281187 A1 | 12/2006 | Emery et al. |
| 2007/0007183 A1 | 1/2007 | Schulat et al. |
| 2007/0073590 A1 | 3/2007 | Cosentino et al. |
| 2007/0088271 A1 | 4/2007 | Richards |
| 2007/0173740 A1 | 7/2007 | Chan et al. |
| 2007/0179404 A1 | 8/2007 | Escutia et al. |
| 2008/0139910 A1 | 6/2008 | Mastrototaro et al. |
| 2008/0167578 A1 | 7/2008 | Bryer et al. |
| 2008/0200838 A1 | 8/2008 | Goldberger et al. |
| 2008/0217407 A1 | 9/2008 | Ackermann et al. |
| 2009/0010802 A1 | 1/2009 | Joseph et al. |
| 2009/0050491 A1* | 2/2009 | Brown ....................... 205/777.5 |
| 2009/0138207 A1 | 5/2009 | Cosentino et al. |
| 2009/0171589 A1 | 7/2009 | Kovatchev |
| 2009/0270765 A1 | 10/2009 | Ghesquiere et al. |
| 2009/0322513 A1 | 12/2009 | Hwang et al. |
| 2010/0069730 A1 | 3/2010 | Bergstrom et al. |
| 2010/0087754 A1 | 4/2010 | Rush et al. |
| 2010/0094205 A1 | 4/2010 | Boyd et al. |
| 2010/0151488 A1 | 6/2010 | Smith et al. |
| 2010/0212675 A1 | 8/2010 | Walling et al. |
| 2010/0218132 A1 | 8/2010 | Soni et al. |
| 2010/0262380 A1* | 10/2010 | Matievich et al. ............... 702/22 |
| 2010/0270149 A1 | 10/2010 | Wang et al. |
| 2010/0286563 A1 | 11/2010 | Bryer et al. |
| 2010/0312137 A1 | 12/2010 | Gilmour et al. |
| 2010/0317935 A1 | 12/2010 | Roe et al. |
| 2010/0331653 A1 | 12/2010 | Stafford |
| 2011/0009775 A1 | 1/2011 | Roe |
| 2011/0040165 A1 | 2/2011 | Williams, III |
| 2011/0054390 A1 | 3/2011 | Searle et al. |
| 2011/0118771 A1 | 5/2011 | Ruan et al. |
| 2011/0124130 A1 | 5/2011 | Wagner et al. |
| 2011/0124996 A1 | 5/2011 | Reinke et al. |
| 2011/0132759 A1 | 6/2011 | Petyt et al. |

FOREIGN PATENT DOCUMENTS

| | | |
|---|---|---|
| CA | 2544953 | 10/2006 |
| CA | 2599573 | 11/2006 |
| CA | 2607437 | 12/2006 |
| CA | 2646279 | 10/2007 |
| CA | 2669302 | 6/2008 |
| CA | 2327127 | 8/2010 |
| EP | 1399059 | 8/2006 |
| EP | 1717942 | 11/2006 |
| EP | 1328192 | 1/2011 |
| EP | 2284747 | 2/2011 |
| EP | 1664783 | 5/2011 |
| EP | 2195050 | 5/2011 |
| WO | WO 9935487 A1 * | 7/1999 |
| WO | 02/094092 | 11/2002 |
| WO | 03/047426 | 6/2003 |
| WO | 2006/122741 | 11/2006 |
| WO | 2006/133435 | 12/2006 |
| WO | 2007/112034 | 10/2007 |
| WO | 2008069932 | 6/2008 |
| WO | 2009146379 | 12/2009 |
| WO | 2010009870 | 1/2010 |
| WO | 2010049669 | 5/2010 |
| WO | 2010054205 | 5/2010 |
| WO | 2010068617 | 6/2010 |
| WO | 2010120563 | 10/2010 |
| WO | 2010134969 | 11/2010 |
| WO | 2011008520 | 1/2011 |

| | | |
|---|---|---|
| WO | 2011/019657 | 2/2011 |
| WO | 2011/026053 | 3/2011 |
| WO | 2011/060923 | 5/2011 |

OTHER PUBLICATIONS

* "Always Connected, Always Monitoring the Critical Signals You Need to Know", CST Critical Signal Technologies, your Link to Life, Farmington Hills, MI 48335.

* Amy T., "Lifescan's New Diabetes iPhone App", Diabetes Mine: the all things diabetes blog, Mar. 17, 2009, http://www.diabetesmine.com/2009/03/lifescans-new-diabetes-iphone-app.html.

* "Medline Docking Station for Glucose Meter", http://www.google.com/products/catalog?q=docking+station+for+glucose+meter&hl=en&um=1&ie=UTF-8&tbm=shop&cid=14673613440805108352&sa=X&ei=Eq-DTp2QGcnKiALyt-XwBw&ved=0CFIQ8w1wAA#.

* "OneTouch Ultra Link" Lifescan Consumer Products, 2011, http://www.lifescan.com/products/meters/ultralink/.

* "Precision PCx Glucose Monitoring System—Medline and Abbott Diabetes Care Post Acute Care Bring You Fill Billing Capture, Compliance, and Accuracy in Blood Glucose Testing", Med Supplies Care, 2011, http://www.medsuppliescare.com/medsupply.cfm/DOCKING-STATION-FOR-PRECISION-PCX-5650.

* "TRUEmanager—Track a healthier course to diabetes management", Nipro Diagnostics, 2010, http://www.niprodiagnostics.com/our_products/ma_true_manager.aspx.

* "TRUEresult Docking Station and USB Cable", Diabetes Health Supplies, 2011, http://www.diabeteshealthsupplies.com/products/TRUEresult-Docking-Station-and-USB-Cable.html.

* cited by examiner

TEST UNIT CARTRIDGE FOR ANALYTE TESTING DEVICE

This application is a continuation of U.S. patent application Ser. No. 13/187,397 filed Jul. 20, 2011, which is a continuation-in-part of U.S. patent application Ser. No. 13/165,621 filed Jun. 21, 2011, which are incorporated herein by reference in its entirety.

FIELD OF THE INVENTION

The field of the invention is analyte testing supplies, more specifically, test unit cartridges.

BACKGROUND

Analyte testing devices play a critical roll in modern diagnosis and management of health-related issues. For example, a sample of human blood, urine, and/or saliva can be tested for glucose, fructosamine, hematocrit, hemoglobin blood oxygen saturation, lactates, iron, pH, cholesterol, liver enzymes (AST, ALT, alkaline phosphatase/GGT, LDH, bilirubin, etc), hormones, and other compounds.

For many diabetic patients, monitoring glucose levels is inconvenient and uncomfortable, since it requires repeatedly pricking the finger or some other body member in order to draw a blood sample. It would be advantageous to maximize the utility of a blood sample by collecting more than one kind of health data using the same meter, and even more preferably from the same "stick". For example, while a diabetes patient is primarily concerned with monitoring glucose levels, it would be advantageous for diabetic patients to simultaneously, or in close time proximity, collect pH, iron, fructosamine or other health data. Such additional health data can be used as a baseline for later medical reference, or alternatively, for proactively monitoring for other potential health problems.

Several known references are directed at a single test unit that simultaneously tests for two or more analytes. For example, each of U.S. Pat. No. 7,955,791 (Dinello), US20110124130 (Wagner), and US2010/0312137 (Gilmour) disclose test strips that test for two or more analytes using one strip. However, none of those references teach a cartridge (i.e., a magazine, cassette or other housing or enclosure) for holding two or more non-fungible test units.

US 2007/0007183 to Schulat discloses a magazine that holds a plurality of test units for measuring analytes like glucose. However, Schulat fails to contemplate that a magazine can hold test units that test for different analytes.

US 2010/0151488 to Smith discloses a test unit (referred to as a cassette) that has two test spots, i.e., two analyte sensors. One is for measuring glycated albumin, and the other is for measuring total albumin (for diabetes management). Smith, however, still does not contemplate a cassette that carries two or more different types of test units (i.e., non-fungible test units).

Thus, while known prior art has appreciated the advantages of a test unit that tests for two or more analytes, the known prior art has failed to provide a cartridge for holding a plurality of test units, wherein at least two of the test units are non-fungible (e.g., a first test unit configured to detect a first analyte and a second test unit configured to test a second analyte that is different from the first analyte). It would therefore be advantageous to provide a cartridge that includes different test units for detecting different analytes. For example, an inventive cartridge holding twenty separate test units could include glucose-detecting analyte sensors on every test unit, and fructosamine-detecting analyte sensors on every fifth test unit (i.e., every fifth test unit has two analyte sensors). Furthermore, it would be advantageous for that device to automatically store and monitor both glucose and fructosamine levels. In this manner, a diabetic patient primarily concerned with glucose levels could simultaneously collect other important health data, thus maximizing the utility of each blood sample.

Thus, there is still a need for test unit cartridges that include non-fungible test units.

SUMMARY OF THE INVENTION

The inventive subject matter provides apparatus, systems, and methods in which a test unit cartridge houses: (i) a first test unit having a first analyte sensor that includes a first reagent used to detect a first analyte; and (ii) a second test unit having a second analyte sensor that includes a second reagent used to detect a second analyte different from the first analyte, such that the first test unit is not functionally fungible with the second test unit.

In one aspect of some preferred embodiments, the test unit comprises a single strip. As used herein, the term "strip" means a thin (less than 5 mm thick) elongated object having at least one analyte sensor. A test unit can also comprise a non-strip configuration, such as a capsule more that 5 mm thick, or a disk.

In yet other aspects of preferred embodiments, the first test unit has no other analyte sensors besides the first analyte sensor. Alternatively, the first test unit can include an additional analyte sensor that detects the second analyte.

In another aspect of some preferred embodiments, the cartridge includes a "sacrificial" test unit disposed at a beginning of an order of use of the cartridge. The sacrificial test unit is configured to provide a moisture barrier by corking and sealing all apertures of the cartridge. The "sacrificial" test unit can optionally include at least two analyte sensors for detecting multiple analytes. It is also contemplated that each test unit can include features that cork the apertures of the cartridge such that the test units are protected from moisture and dust when not in use.

In one aspect of preferred embodiments, the test unit cartridge includes a third through twentieth test unit, each of which is functionally fungible with the first test unit.

In yet other aspects of preferred embodiments, the first reagent and second reagent are different. For example, the first reagent is configured to bind with a first analyte and the second reagent is configured to bind with a second analyte.

In some aspects of preferred embodiments, the cartridge includes pull-away labels that cover every aperture of the cartridge in order to provide a seal and barrier from moisture and dust.

In yet other aspects, the cartridge includes an aperture that allows an electrical contact of the first test unit to directly couple with an electrical contact of an analyte testing device.

The inventive subject matter also provides apparatus, systems, and methods in which a test unit cartridge has a plurality of test units, wherein at least one of the test units has a first and second analyte sensor configured to detect a first and second analyte, respectively. The first and second analyte sensors can be completely non-overlapping, partly overlapping, or completely overlapping. In some aspects of preferred embodiments, the first and second analyte sensors are physically separated by a distance.

Yet still, the inventive subject matter provides apparatus, systems, and methods in which a test unit cartridge includes a calibration test unit and an operating test unit. As used herein, the term "calibration test unit" means a test unit having a known analyte presence and configured to test the accuracy of an analyte testing device (e.g., glucose meter). As used herein, the term "operating test unit" means a test unit having an analyte sensor that is configured to detect an analyte.

The inventive subject matter also provides apparatus, systems, and methods in which a test unit cartridge has a plurality of test units and a spring. The spring is disposed in a manner such that each test unit is advanced into a usable position after a previous test strip has been laterally ejected from the cartridge.

The inventive subject matter also provides apparatus, systems, and methods in which a test unit cartridge houses a plurality of test units in a stacked configuration.

From a method perspective, an analyte testing device can be used by: (i) inserting a lancet cartridge into the device; (ii) inserting a test unit cartridge into the device, wherein the test unit cartridge has a plurality of nonfungible test units; (iii) operating a mechanically advantaged actuator on the device, which operates a mechanism that (a) readies a lancing device, (b) exposes an analyte sensor of a test unit, and (c) advances the lancet cartridge; (iv) deploying the lancing device in order to prick a body part and draw a blood sample; and (v) contacting the analyte sensor to the blood sample.

Preferred methods further include reading an output of the device; ejecting and disposing of the test unit; replacing the lancet cartridge with a refill lancet cartridge; and replacing the test unit cartridge with a refill test unit cartridge. In addition, the nonfungible test units preferably comprise at least one test unit configured to detect a first and second analyte.

Various objects, features, aspects, and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
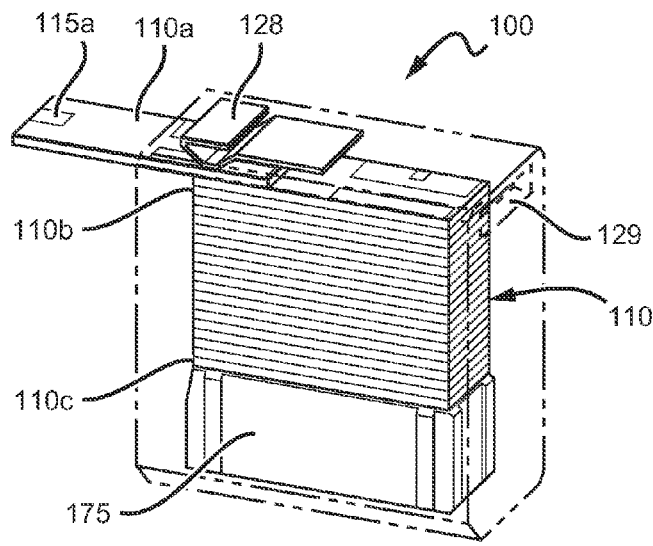
FIG. 1 is a perspective view of one embodiment of a test unit cartridge for housing a plurality of test units.
Figure 2:
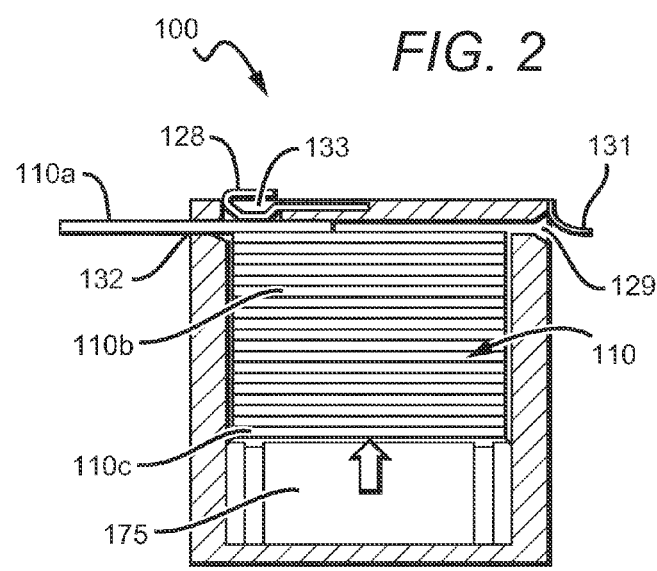
FIG. 2 is a side view of the test unit cartridge of FIG. 1.

FIGS. 1 and 2 show perspective and side views, respectively, of a test unit cartridge 100. Cartridge 100 holds a plurality of test units 110 in a stacked configuration. The stacked configuration of test units 110 advantageously allows cartridge 100 to have a compact and simple design that requires minimal material. Cartridge 100 is configured to couple with an analyte testing device. For example, cartridge 100 has electrical contacts 128 for communicatively coupling the test units 110 with conversion electronics in an analyte testing device. Cartridge 100 also has a slot 129 that couples with a linkage mechanism of an analyte device, wherein the linkage is configured to push a portion of a test unit out of cartridge 100 in order to expose analyte sensor 115. Cartridge 100 is preferably sized and dimensioned to mate with a compartment of an analyte testing device.

Cartridge 100 can include any appropriate number of test units, preferably between 15 and 25 test units, more preferably between 18 and 22 test units, and most preferably 20 test units. Cartridge 100 includes test units configured to test for different analytes. For example, test unit 110$a$ has an analyte sensor 115$a$, which includes an analyte-binding reagent configured to test for glucose. Test unit 110$b$ has two analyte sensors (sensor 115$b$ and sensor 116$b$) for detecting two different analytes (e.g., glucose and iron) using only one fluid sample. Cartridge 100 also has a calibration test unit 110$c$ that has two analyte sensors: sensor 115$c$ is for detecting glucose and calibration sensor 116$c$ is for checking the accuracy of an analyte meter.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Cartridge 100 can include a test unit that is functionally fungible with 110$b$ or 110$c$ at every $n^{th}$ test unit within the plurality of test units 110 in order to ensure that certain health data is gathered at particular intervals. For example, in one preferred embodiment cartridge 100 holds twenty test units, wherein the first and third through twentieth test units are configured to detect glucose, and the second test unit is configured to detect glucose and fructosamine. In this manner, fructosamine levels are monitored at every second test unit of every test unit cartridge.

The housing of cartridge 100 can be made of plastic, metal, composite, or any other material with structural and mechanical properties suitable for housing a plurality of test units. Cartridge 100 is preferably compact, with a height no more than 25 mm, a width no more than 15 mm, and a length no more than 50 mm. In especially preferred embodiments, the height is no more than 20 mm, a width is no more than 8 mm, and a length is no more than 40 mm.

Cartridge 100 also preferably includes an inner desiccant liner (not shown) for protecting the plurality of test units from exposure to moisture. For example, a liner can be disposed between the test units and the inner wall of cartridge 100, thus surrounding all the test units (e.g., an inner sleeve). In some embodiments, the liner comprises a crystalline structure configured to absorb moisture and prevent moisture from reaching the analyte sensors. Liners are well known and all materials suitable for absorbing and/or blocking moisture are contemplated. In addition, all cartridge apertures are preferably sealed with a pull-away adhesive label. For example, pull-away label 131 has been placed over slot 129 in order to seal slot 129, thus protecting test units 110 from exposure to moisture and dust. Preferably, slot 132, slot 133 and all other orifices/apertures of cartridge 100 are sealed with a pull-away label. The labels can be removed just prior to loading cartridge 100 into device 600 (see FIG. 6). Cartridge 100 also preferably includes gaskets and/or o-rings at all cartridge apertures. These gaskets can be configured to mate with components of device 600 such that a seal is maintained while cartridge 100 is loaded in device 600 and not in use.

Cartridge 100 also includes a spring 175, which is disposed below the plurality of test units 110 and is configured to push the test units 110 upward. In this manner, each test unit is pushed up into a usable position after the previous test unit is laterally ejected out of slot 132.

Cartridge 100 provides several advantages. First, by providing a plurality of test units in one disposable and replaceable cartridge, methods and devices for monitoring analytes is significantly simplified. Second, cartridge 100 provides a means for ensuring that secondary health data is gathered at predetermined intervals. For example, a diabetes patient monitoring glucose levels (i.e., primary health data) will nonetheless monitor secondary health data (e.g., fructosomine levels) when test unit 110*b* is used. Third, cartridge 100 allows primary and secondary health data to be gathered simultaneously in a single blood sample. Fourth, cartridge 100 provides an enclosure that protects a plurality of test units from exposure to moisture and dust. Finally, cartridge 100 provides a simple mechanism for advancing each test unit into place after the previous test unit has been removed and disposed.

Figure 3:
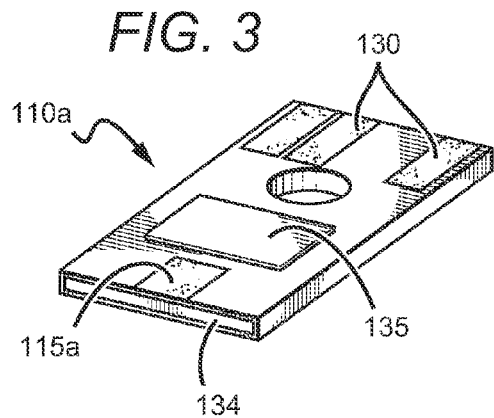
FIG. 3 is a perspective view of one embodiment of a test unit.

FIG. 3 shows a test unit 110*a*, which has an analyte sensor 115*a*. Analyte sensors are well known and generally comprise an absorbent material that includes a reagent (e.g., an analyte-binding reagent). In this case, sensor 115*a* is configured to detect glucose. The sensor 115*a* is configured to generate a signal that is sent to electrical contacts 130. Electrical contacts 130 are communicatively coupled with electrical contacts 128 of cartridge 100, thus allowing the signal to reach conversion electronics in an analyte testing device (e.g., a glucose meter). Alternatively, electrical contacts 130 could directly interface with an analyte testing device's conversion electronics via an open aperture on cartridge 100 (e.g., slot 133 with contacts 128 removed). In this manner, test unit 110*a* allows a diabetic patient to monitor glucose levels. As used herein, "analyte sensor" refers to an independently interpretable signal representing an amount of an analyte present in a fluid sample. Under this definition, one piece of absorbent material having one reagent that is capable of binding to two different analytes at the same time, would be considered two separate "analyte sensors" if two independently interpretable signals are produced, regardless of whether the signal is interpreted using two different lead wires or using one lead wire (e.g., one signal having two frequency spikes that represent the amount of two different analytes present in the fluid sample).

Test unit 110*a* also advantageously includes a first sealing surface 134 and a second sealing surface 135, configured to restrict entry of moisture into the interior of cartridge 100 via slots 132 and 133, respectively. Test unit 110*a* is disposed at the beginning of the order of use of the plurality of test units 110 in cartridge 100 (i.e., on top of the stack of test units 110, see FIG. 1). As such, test unit 110*a* serves to protect the plurality of test units 110 from damage caused by moisture and dust. Test unit 110*a* can either be a "sacrificial unit," meaning its sole purpose is to provide a cork/seal to the orifices of cartridge 100, or can optionally include analyte sensors, such as analyte sensor 115*a*. Test unit 110*a* also preferably includes a sealing surface on its back side to provide a seal at slot 129. It is also contemplated that each of the plurality of test units 110 can include sealing surfaces to protect each subsequent test unit from moisture.

While FIG. 3 shows test unit 110*a* having a "strip" configuration, those of skill in the art will appreciate that other shapes can be used consistently with the inventive subject matter disclosed herein. For example, test unit 110*a* could comprise a capsule or a disk rather than a strip. However, stackable test units are preferred in order to conserve space.

Figure 4:
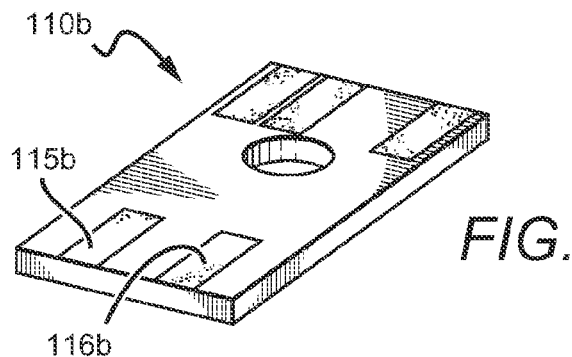
FIG. 4 is a perspective view of another embodiment of a test unit.

FIG. 4 shows a test unit 110*b*, which has two analyte sensors 115*b* and 116*b*. Sensor 115*b* is configured to detect glucose, while sensor 116*b* is configured to detect fructosamine. Test unit 110*b* advantageously provides a means for testing for two analytes using one blood sample (i.e., from a single prick and a single test unit). While FIG. 4 shows sensors 115*b* and 116*b* in completely non-overlapping positions, it is also contemplated that sensors 115*b* and 116*b* could be partially overlapping, or even completely overlapping. For example, sensors 115*b* and 116*b* could comprise one absorbent material and one analyte-binding reagent, wherein the analyte-binding reagent is capable of simultaneously binding with two or more analytes and can produce two "distinct" signals (e.g., one signal with two different detectible frequency spikes, or two different signals representing two distinct analytes). One of skill in the art will also appreciate that additional sensors can be included on test unit 110*b* for detecting additional analytes.

Test unit 110*a* and test unit 110*b* are "functionally nonfungible" since unit 110*a* tests for glucose while unit 110*b* detects glucose and fructosamine. An example of two functionally fungible test units is a first test unit that test for glucose and iron, and a second test unit that tests for glucose and iron.

Figure 5:
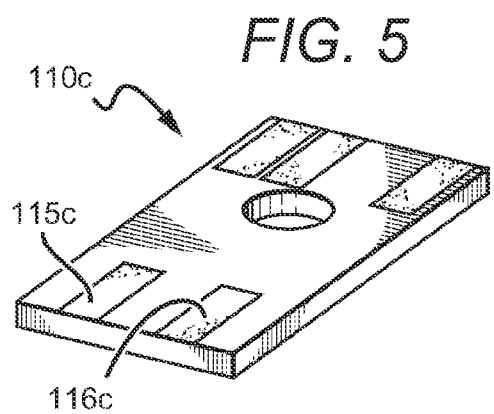
FIG. 5 is a perspective view of a calibration test unit.

FIG. 5 shows a test unit 110*c*, which has two analyte sensors 115*c* and 116*c*. Sensor 115*c* is configured to detect glucose, while calibration sensor 116*c* is configured to check the accuracy of an analyte testing device. As such, sensor 115*c* is an "operational sensor" and sensor 116*c* is a "calibration sensor." Sensor 116*c* has a known concentration of a particular analyte and produces a signal that is expected to result in a known reading on device 600. In this manner, the electronics of device 600 can be checked for accuracy, precision, and consistency.

Figure 6:
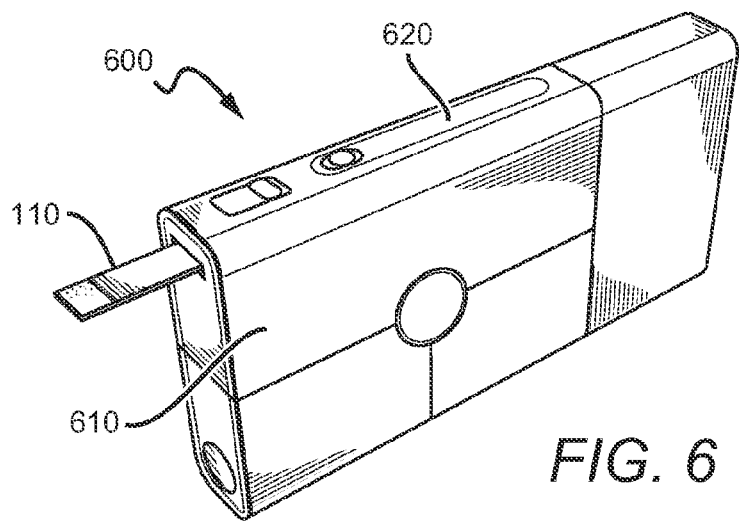
FIG. 6 is a perspective view of one embedment of an analyte testing device.

FIG. 6 shows an analyte testing device 600. Device 600 is a glucose meter integrated with a lancing device. Device 600 has an actuator 620 and an internal linkage mechanism (not shown) configured to cock a lancet for drawing blood, partially expose a test unit for contacting with a blood sample, and reading a signal of the test unit. Device 600 also has an internal compartment 610 for loading and storing cartridge 100. Device 600 also preferably has an internal compartment for storing a cartridge of lancets (not shown). One exemplary embodiment of a glucose meter is disclosed in patent application Ser. No. 13/165,621, which is incorporated herein by reference.

Device 600 can further include a docking station and data management software. Acceptable docking stations and data management systems that could be adapted for use within the existing subject matter is described in co-pending patent application having serial number 13/187,360 titled to Shaanan et al. "Analyte Testing System With Docking Station For Data Management" filed on Jul. 20, 2011.

Figure 7:
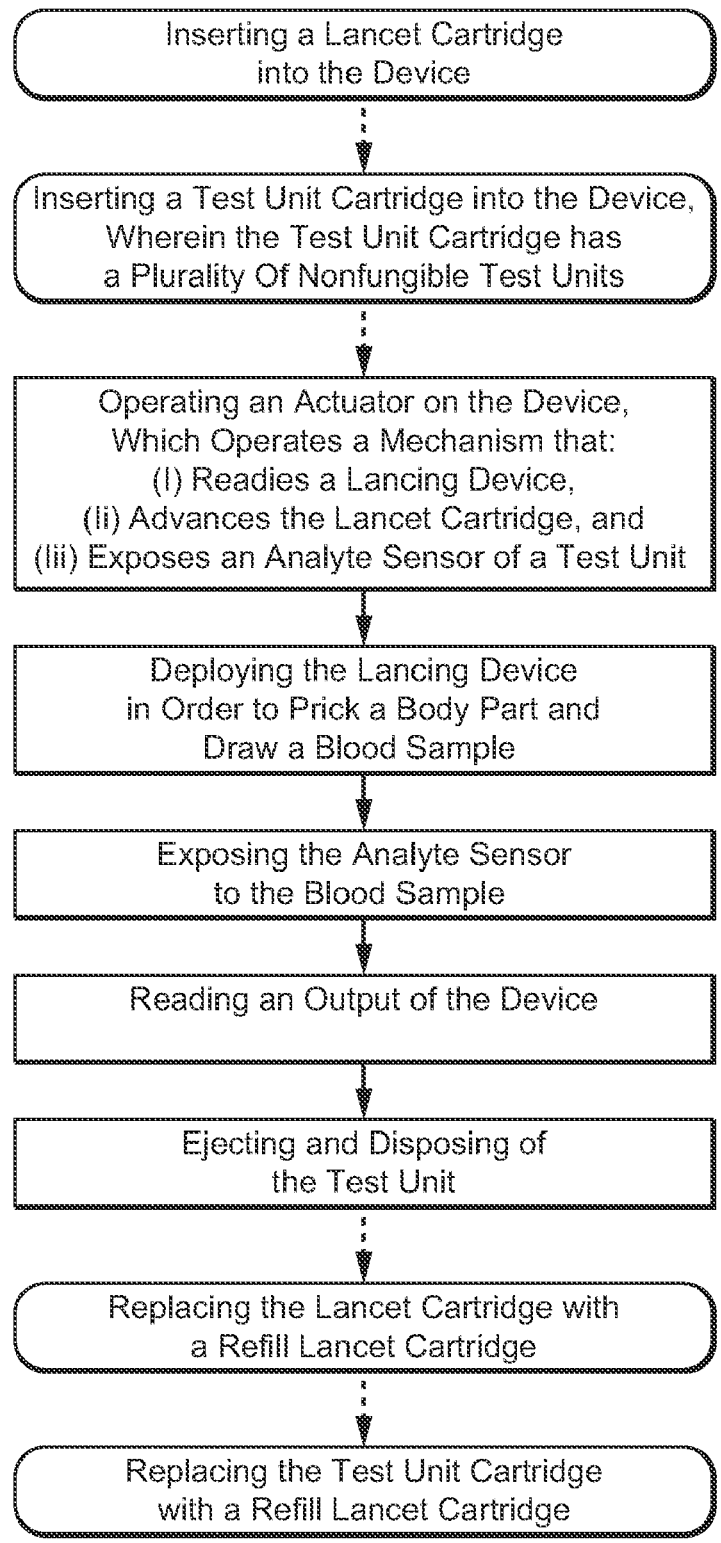
FIG. 7 is a schematic of one embodiment of a method of using the test unit cartridge of FIG. 1.

FIG. 7 shows a method of using test cartridge 100 and analyte testing device 600, comprising: inserting a lancet cartridge into the device; inserting a test unit cartridge into the device, wherein the test unit cartridge has a plurality of non-fungible test units; operating an actuator on the device, which operates a mechanism that (i) readies a lancing device, (ii) advances the lancet cartridge, and (iii) exposes an analyte sensor of a test unit; deploying the lancing device in order to prick a body part and draw a blood sample; and exposing the analyte sensor to the blood sample; reading an output of the device; ejecting and disposing of the test unit; replacing the lancet cartridge with a refill lancet cartridge; and replacing the test unit cartridge with a refill test unit cartridge. Indicia of the first two and last two steps are displayed in round boxes and with dotted lines to indicate that these steps need not be repeated at every cycle of usage of the device. For example, in embodiments having twenty lancets and test units per cartridge, the steps of inserting/removing cartridges need only be performed every twentieth cycle of use. In addition, the non-fungible test units preferably comprise at least one test unit configured to detect a first and second analyte.

In one aspect of some preferred embodiments, the actuator is mechanically advantaged and the step of operating the actuator comprises cocking a lever.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A test unit cartridge comprising:
   a first test unit type having a first analyte sensor that includes a first reagent used to detect a first analyte; and
   a second test unit type having a second analyte sensor that includes a second reagent used to detect a second analyte different from the first analyte, such that the first test unit type is not functionally fungible with the second test unit type, wherein
   the first test unit type and the second test unit type are arranged in a stacked configuration within the test unit cartridge as a plurality test units;
   the first test unit type is situated at first positions within the stacked configuration and used to detect the first analyte, and
   the second test unit type is situated at second positions within the stacked configuration and used to detect the second analyte so as to allow detection of the first analyte and the second analyte at a predetermined interval.

2. The cartridge of claim 1, wherein the first test unit type comprises a strip.

3. The cartridge of claim 1, wherein the first test unit type has no other analyte sensors besides the first analyte sensor.

4. The cartridge of claim 1, wherein the first test unit type comprises a third analyte sensor that detects the second analyte.

5. The cartridge of claim 4, wherein the first and third analyte sensors are physically separated by a distance.

6. The cartridge of claim 1, wherein test unit disposed at a beginning of an order of use of the cartridge is of the first test unit type, and has a sealing surface that cooperates with a housing of the cartridge to restrict entry of moisture into the cartridge.

7. The cartridge of claim 1, further comprising a third through a twentieth test units, each of which is functionally fungible with one of the first and second test units.

8. The cartridge of claim 1, wherein the second reagent is different from the first reagent.

9. The cartridge of claim 1, further comprising a pull-away label covering an aperture of the cartridge.

10. The cartridge of claim 1, further comprising an aperture disposed on the cartridge such that an electrical contact of test unit disposed at a beginning of an order of use of the cartridge can directly couple with an electrical contact of an analyte testing device.

11. The cartridge of claim 1, further comprising a calibration test unit.

12. The cartridge of claim 1 further comprising a spring disposed in a manner to advance each test unit into a usable position after a previous test unit has been laterally ejected from the cartridge.

* * * * *